United States Patent
Neckernuss et al.

(10) Patent No.: US 12,422,657 B2
(45) Date of Patent: Sep. 23, 2025

(54) APPARATUS AND METHOD FOR DETECTING A SPATIAL ELONGATION OF AT LEAST ONE ADHERENT BIOLOGICAL CELL

(71) Applicant: UNIVERSITÄT ULM, Ulm (DE)

(72) Inventors: Tobias Neckernuss, Eislingen (DE); Daniel Geiger, Mittelbiberach (DE); Othmar Marti, Ulm (DE)

(73) Assignee: Universität Ulm, Ulm (DE)

( * ) Notice: Subject to any disclaimer, the term of this patent is extended or adjusted under 35 U.S.C. 154(b) by 1189 days.

(21) Appl. No.: 17/270,014

(22) PCT Filed: Aug. 20, 2019

(86) PCT No.: PCT/EP2019/072212
§ 371 (c)(1),
(2) Date: Sep. 14, 2021

(87) PCT Pub. No.: WO2020/038914
PCT Pub. Date: Feb. 27, 2020

(65) Prior Publication Data
US 2022/0214331 A1    Jul. 7, 2022

(30) Foreign Application Priority Data
Aug. 20, 2018 (DE) .................... 10 2018 213 965.2

(51) Int. Cl.
*G02B 21/06* (2006.01)
*C12M 1/42* (2006.01)
*G01N 15/14* (2024.01)

(52) U.S. Cl.
CPC ............. *G02B 21/06* (2013.01); *G01N 15/14* (2013.01); *C12M 35/02* (2013.01); *G01N 2015/1495* (2013.01)

(58) Field of Classification Search
CPC ........ G02B 21/06; G02B 21/32; G01N 15/14; G01N 2015/1495; G01N 2015/1006; C12M 35/02; C12M 41/46
See application file for complete search history.

(56) References Cited

U.S. PATENT DOCUMENTS

| 6,067,859 A | 5/2000 | Käs et al. |
| 6,850,363 B1 | 2/2005 | Wedenburg et al. |

(Continued)

FOREIGN PATENT DOCUMENTS

| DE | 19954933 A1 | 5/2001 |
| EP | 1 469 483 A2 | 10/2004 |

OTHER PUBLICATIONS

U.S. Appl. No. 16/479,689, filed Jul. 22, 2019, Pending.
(Continued)

*Primary Examiner* — William H. Beisner
*Assistant Examiner* — Danielle B Henkel
(74) *Attorney, Agent, or Firm* — Leydig, Voit & Mayer, Ltd.

(57) ABSTRACT

An apparatus for detecting a spatial elongation of at least one adherent biological cell is provided. The apparatus contains at least one biological cell, which is adhered to a substrate, a laser for irradiating the at least one biological cell for a spatial elongation of the cell in a direction parallel to the irradiation direction and a detector for detecting the spatial elongation of the cell in the direction parallel to the radiation direction. Further, a corresponding method for spatial elongation of an adherent biological cell is provided and the uses of the apparatus and of the method proposed. Using the apparatus and method, it is possible to ascertain, from parts of adherent cells to entire groups of adherent cells, the (Continued)

mechanical properties in the natural, adherent state of the cell(s) in spatially selective, temporally selective and contactless fashion.

17 Claims, 1 Drawing Sheet

(56) References Cited

U.S. PATENT DOCUMENTS

| | | | |
|---|---|---|---|
| 8,076,632 B2* | 12/2011 | Kreysing | B03C 5/026 250/251 |
| 8,119,976 B2* | 2/2012 | Squier | G21K 1/006 435/173.9 |
| 8,149,416 B2* | 4/2012 | Akcakir | G01B 9/021 356/457 |
| 9,683,982 B2* | 6/2017 | Käs | G01N 33/5011 |
| 9,885,644 B2* | 2/2018 | Sawetzki | G01N 3/02 |
| 2004/0209281 A1 | 10/2004 | Monajembashi | |
| 2007/0008528 A1* | 1/2007 | Chiou | G01N 15/1433 356/601 |
| 2007/0086919 A1* | 4/2007 | Akcakir | G01N 21/6456 422/82.05 |
| 2007/0119714 A1* | 5/2007 | Schnelle | G01N 15/1023 204/547 |
| 2013/0230879 A1 | 9/2013 | Neeves et al. | |
| 2014/0366638 A1* | 12/2014 | Sawetzki | G02B 21/32 73/788 |
| 2015/0077869 A1* | 3/2015 | Meng | G02B 27/0966 359/837 |
| 2018/0188173 A1 | 7/2018 | Scarcelli et al. | |
| 2020/0230602 A1* | 7/2020 | Yao | B01L 3/50273 |
| 2021/0325293 A1* | 10/2021 | Geiger | G06T 7/269 |
| 2022/0214331 A1* | 7/2022 | Neckernuss | C12M 41/46 |

OTHER PUBLICATIONS

Ermilov et al., "Measurements of cell wall mechanical properties using optically trapped fluorescent microspheres," *Proceedings of SPIE* 5514: 189-196 (2004)—Abstract only.

Nawaz et al., "Cell visco-elasticity measured with AFM and optical trapping at submicrometer eformation," *PLOS One* 7(9): e45297 (2012)—9 pgs.

Sen et al., "Combining mechanical and optical approaches to dissect cellular mechanobiology," *Journal of Biomechanics* 43(1): 45-54 (2010)—Abstract only.

Thoumine et al., "Time scale dependent viscoelastic and contractile regimes in fibroblasts probed by microplate manipulation," *Journal of Cell Science* 110(17): 2109-2116 (1997).

German Patent Office, Office Action in German Patent Application No. 10 2018 213 965.2 (Aug. 22, 2019).

European Patent Office, International Search Report in International Application No. PCT/EP2019/072212 (Dec. 6, 2019).

European Patent Office, Written Opinion in International Application No. PCT/EP2019/072212 (Dec. 6, 2019).

International Bureau of WIPO, International Preliminary Report on Patentability in International Application No. PCT/EP2019/072212 (Feb. 23, 2021).

* cited by examiner

Figure 1A
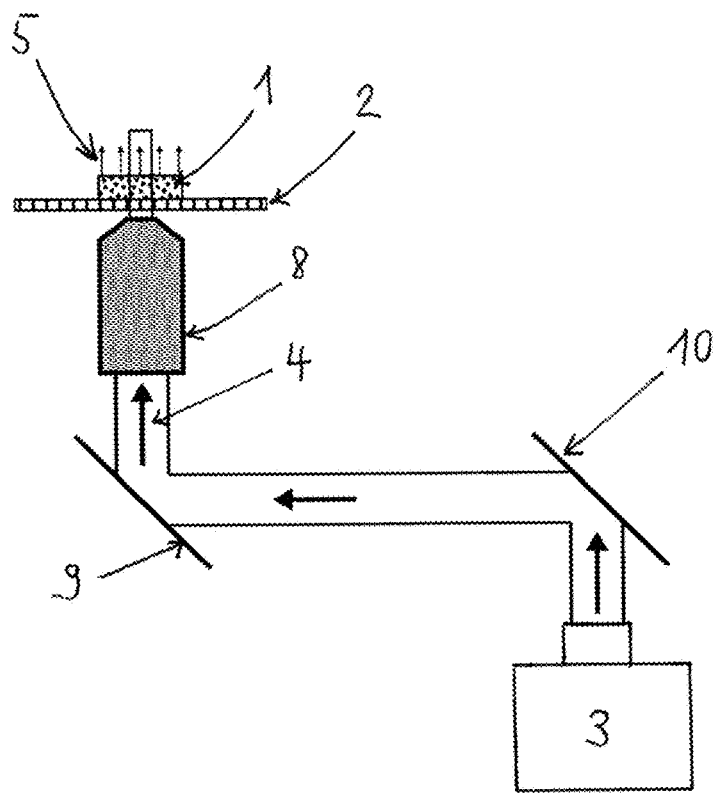
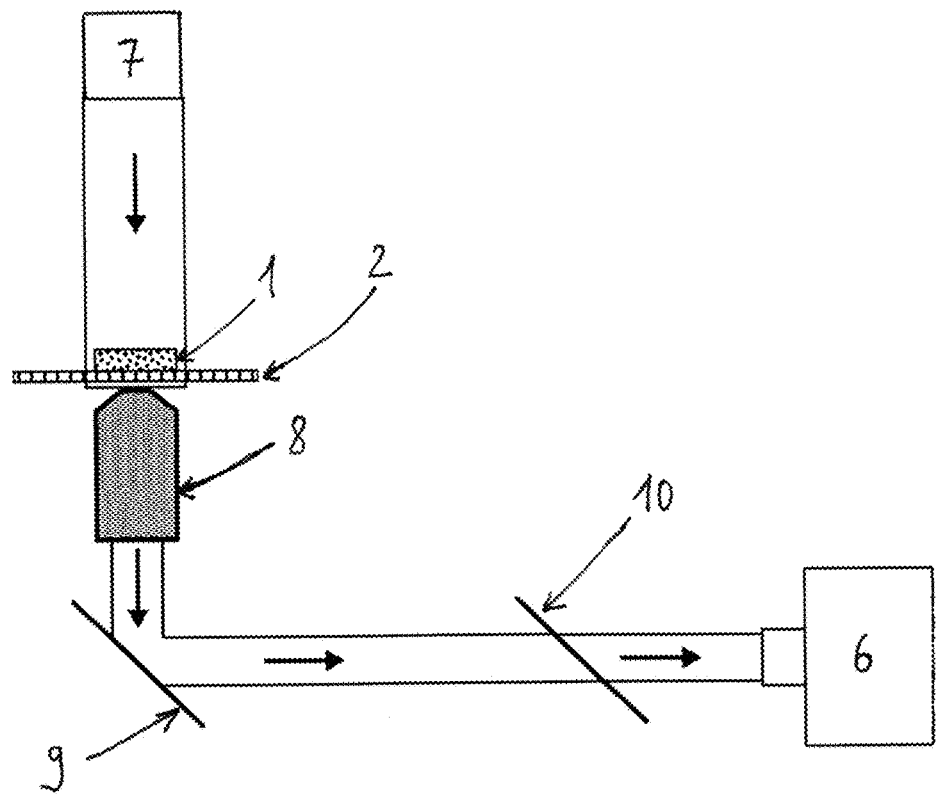
Figure 1B

APPARATUS AND METHOD FOR DETECTING A SPATIAL ELONGATION OF AT LEAST ONE ADHERENT BIOLOGICAL CELL

CROSS-REFERENCE TO RELATED APPLICATIONS

This patent application is the U.S. national phase of International Application No. PCT/EP2019/072212, filed on Aug. 20, 2019, which claims the benefit of German Patent Application No. 10 2018 213 965.2, filed Aug. 20, 2018, the disclosures of which are incorporated herein by reference in their entireties for all purposes.

An apparatus for detecting a spatial elongation of at least one adherent biological cell is provided. The apparatus comprises at least one biological cell that is adherent on a substrate, a laser for irradiating the at least one biological cell for the spatial elongation of the cell in a direction parallel to the direction of irradiation, and a detector for detecting the spatial elongation of the cell in a direction parallel to the direction of irradiation. A corresponding method for the spatial elongation of an adherent biological cell is furthermore provided and the uses of the apparatus and of the method are proposed. It is possible with the apparatus and the method to determine the mechanical properties of parts of adherent cells up to whole groups of adherent cells in a spatially selective, temporally selective, and contactless manner in the natural, adherent state of the cells(s).

A large number of methods of examining the mechanical properties of adherent biological cells are known in the prior art. Examples for this are atomic force microscopy, micropipetting, an optical trap, and the mechanical stretching of the substrate.

It is disadvantageous in atomic force microscopy, in micropipetting, and in the mechanical stretching of the substrate that the stretching force on the biological cells is exerted via establishment of a contact with the biological cells, that is, to a certain degree, in an "invasive" manner. It is disadvantageous in this context that the contact locally exerts a high force at a specific surface of a cell, whereby the cell can be damaged during the measurement and the measurement can be falsified.

With the contactless measurement of the mechanical properties of biological cells with the optical stretchers known in the prior art is connected the disadvantage that the cells have to be suspended in a liquid medium (e.g. an aqueous buffer) for the generation of the stretching.

For example, from U.S. Pat. No. 6,067,859 A, a measurement method is known in which biological cells suspended in an aqueous medium undergo a so-called optical stretching via the effect of electromagnetic radiation and mechanical properties of the cells are derived therefrom. For said measurement, it is necessary to immobilize the biological cell to be examined via electromagnetic radiation from two oppositely disposed irradiation sources (e.g. lasers), i.e. to "capture" them at the location at which the oppositely directed electromagnetic radiation impacts the respective opposite sides of the biological cell. Since the refractive index of the aqueous medium in which the cells are suspended is smaller than the refractive index of the cells, the electromagnetic radiation acting on the suspended cell(s) effects a stretching of the suspended cell(s) in two opposite directions along a straight line that coincides with the optical axis of the two oppositely disposed radiation sources. Mechanical properties of the biological cells can be derived via the speed and the degree of stretching.

The disadvantage of the optical stretcher for suspended cells is that no spatial elongation of adherent biological cells is detectable by it. In the case of a measurement of cells that are characterized by adherent growth (e.g. fibroblasts), for a detection of the spatial elongation of these cells via this method, it is necessary to separate the adherent cells (e.g. via the effect of the enzyme trypsin) from the substrate on which they are cultivated prior to the measurement, and to resuspend them in a liquid (e.g. a buffer). Since the separation of these cells from the substrate changes the mechanical properties of these cells in comparison with their natural, adherent status, it is only possible with this method to detect the mechanical properties of these cells in a suspended state, that is in a state that differs from their natural, adherent state in vivo.

A further disadvantage of the measurement using the optical stretcher with suspended cells is that the beam width of the electromagnetic radiation has to be wider than the width of the cell to be examined since the cell to be examined otherwise does not remain captured in a stable manner between the two beams of the opposite electromagnetic radiation. It is consequently not possible with this method to apply a stretching force only at individual points at the surface of a cell to be examined to spatially-selectively derive mechanical properties therefrom at these points.

Starting from this, it was the object of the present invention to provide an apparatus and a method for detecting a spatial elongation of at least one adherent biological cell that does not have the disadvantages of the apparatus and methods known in the prior art. It should specifically be possible with the apparatus or method to simultaneously exert a defined stretching force in a spatially and temporally selective manner on a portion of adherent biological cells, a whole adherent biological cell, or a plurality of adherent biological cells and, in doing so, non-invasively (i.e. contactlessly) exactly determine the degree of elongation of the biological cells(s) to derive mechanical properties of the biological cell(s) therefrom.

The object is achieved by the features of the invention described herein, by the method described herein, and the advantageous developments thereof. Uses according to the invention are also described.

In accordance with the invention, an apparatus for detecting a spatial elongation of at least one adherent cell is provided, comprising a) at least one biological cell on a substrate;
b) a laser for irradiating the at least one biological cell with electromagnetic radiation in a direction of irradiation, wherein the laser is configured to irradiate electromagnetic radiation on the at least one biological cell that effects a spatial elongation of the at least one biological cell in a direction parallel to the direction of irradiation; and
c) a detector for detecting a spatial elongation of the at least one biological cell in a direction parallel to the direction of irradiation;

characterized in that the at least one biological cell is a biological cell adherent on the substrate.

The cells adherent on the substrate have a refractive index (e.g. a refractive index of 1.38) that differs from their environment, i.e. the medium thereunder (e.g. a glass substrate having a refractive index of 1.52) and the medium thereabove (e.g. air having a refractive index of 1.00 or an aqueous buffer having a refractive index of 1.33). The effect of electromagnetic radiation via the laser has the effect that a stretching force that is directed in the direction of the surrounding medium having a lower refractive index (i.e. in the direction of the air or of the aqueous medium) acts on the adherent cells along the optical axis of the radiation. Consequently, the cells are stretched away from the substrate by the laser radiation, wherein the adhesion force of the cells on the substrate prevents that the stretching of the cells effected by the laser radiation results in a separation of the cells from the substrate. The effected spatial elongation or relative height change of the cell remaining adherent on the substrate can be detected via the detector.

It is possible for the first time via the apparatus in accordance with the invention to deform a portion of adherent biological cells, a whole adherent biological cell, or a plurality of adherent biological cells spatially-selectively, temporally-selectively, and without contact to a measurement device via a directly applied stretching force in a direction perpendicular to the substrate and away from the substrate, to detect the degree of deformation, and to derive mechanical properties (e.g. viscoelastic properties via stress-strain curves) of the at least one adherent cell or parts thereof in the natural (i.e. adherent) state of the cell from the degree of deformation.

If the environment of the at least one biological cell turned away from the substrate has a refractive index that is smaller than the refractive index of the cell itself (e.g. air with a refractive index of 1.00 or an aqueous buffer with a refractive index of 1.33), the at least one cell is stretched away from the substrate. If the environment of the at least one biological cell turned away from the substrate has a refractive index that is greater than the refractive index of the cell itself (e.g. glycerin with a refractive index of 1.47), the at least one cell is stretched toward the substrate, i.e. compressed toward the substrate. In both cases, mechanical properties of the at least one adherent cell or parts thereof can be derived by the detected degree of deformation of the at least one adherent cell.

The apparatus in accordance with the invention can be characterized in that the apparatus does not have a laser that is configured to irradiate electromagnetic radiation onto the at least one biological cell in a further direction that has an angle of 180°, optionally an angle in the range from >90° to 180°, to the direction of irradiation.

In a preferred embodiment, the apparatus includes a light source for the irradiation of the at least one biological cell with light in a direction of light irradiation, with the direction of light irradiation preferably being parallel to the direction of irradiation of the laser to the at least one biological cell and/or against the direction of radiation of the laser to the at least one biological cell (i.e. at an angle of 180° to the direction of irradiation of the laser to the at least one biological cell). The light source is preferably selected from the group consisting of light sources of incoherent light, particularly preferably selected from the group consisting of halogen lamp, LED, and combinations thereof.

The apparatus is preferably configured such that the electromagnetic radiation, optionally deflected via a dichroic and/or simple mirror, radiates onto the at least one biological cell (or parts thereof) perpendicular to a surface of the substrate on which the at least one biological cell is located. The dichroic mirror can be suitable to reflect light having a wavelength of >700 nm (e.g. laser light of the wavelength 800 nm) and to allow light having a wavelength of ≤700 nm (e.g. visible light) to pass. The simple mirror can be suitable to reflect visible light and IR light (e.g. light having a wavelength of 400 nm to 800 nm).

In a particularly preferred embodiment, the apparatus is configured such that the electromagnetic radiation radiates through the substrate onto the at least one biological cell (or parts thereof). It is essential in this case that the substrate allows the electromagnetic radiation of the laser to pass at least in part, with the substrate particularly preferably being transparent for the electromagnetic radiation. The substrate can be selected from the group consisting of glass, quartz glass, quartz, transparent plastic (e.g. PMMA or polycarbonate), and combinations thereof.

The apparatus can furthermore be configured to move the laser along a surface of the substrate and/or to move the substrate along a surface of the substrate, preferably along a plane that is parallel to a surface of the substrate. The movement of the substrate can take place via a piezo stage on which the substrate is located.

The apparatus can have a processing unit that is preferably configured to receive and evaluate data of the detector and/or of a data storage of the apparatus, wherein the processing unit is preferably configured to carry out a conversion of the data to a spatial elongation of the at least one cell in an unknown length into a spatial elongation of the at least one cell in a known length, wherein the processing unit is particularly preferably configured to use diffraction images detected at the detector and a (calibrated) point spread function for the conversion and wherein the processing unit is very particularly preferably configured to convert the data on the spatial elongation into a focal height, an E-modulus, and/or a shear modulus of the at least one biological cell.

It is advantageous for a detection of the relative height change of the at least one cell with high sensitivity if the cell membrane of the at least one cell is marked with a substance that has a greater refractive index than the environment of the at least one cell turned away from the substrate (e.g. >1.33 in the case of an aqueous buffer), preferably a refractive index that is greater than the refractive index of the at least one cell (e.g. >1.38). For example, particles can be adhered to the cell membrane of the cell(s) for this purpose. The particles can comprise or consist of, for example, a plastic material, preferably polystyrene (refractive index 1.58). The particles preferably have a mean particle diameter in the range from 1 nm to 10 μm, particularly preferably 10 nm to 5 μm, very particularly preferably 100 nm to 2 μm, in particular 1 μm, measured via dynamic light scattering. The at least one cell is in particular marked by 1 to 10, preferably 2 to 9, particularly preferably 4 to 8, particles. The detection sensitivity of the elongation of the at least one cell can thus be considerably increased since the movement of the particles can be detected via the detector and the movement of the (unmarked) cell membrane does not have to be detected via the detector.

In a preferred embodiment of the apparatus, for the conversion of the relative height change detected by the detector into an absolute height change, the detector is suitable to be calibrated. In this respect, the substrate of the apparatus is preferably movable in a direction parallel to the direction of radiation of the laser, particularly preferably via a piezo stage that the apparatus in accordance with the invention comprises and on which the substrate is arranged. A specific value of the height change can be associated with each detector signal by the movability of the substrate in a direction parallel to the direction of radiation of the laser and the vertical change of the cell(s), that is only qualitative per se, can be quantified (e.g. given in nanometers to micrometers).

In a further preferred embodiment, the apparatus comprises a temperature control unit for tempering the substrate. The temperature control unit is preferably configured to temper the substrate to a temperature in the range from >0° C. to <60° C., preferably 5° C. to 50° C., particularly preferably 10° C. to 45° C., in particular 20° C. to 40° C. The substrate can comprise a channel system through which a cooling fluid of the temperature control unit can flow. The substrate can furthermore have a specific heat capacity of less than 4 J/g·K, preferably less than 3 J/g·K, particularly preferably less than 2 J/g·K, very particularly preferably less than 1 J/g·K, in particular less than 0.5 J/g·K. The lower the specific heat capacity of the substrate, the faster the temperature of the substrate, and thus of the cells adherent to the substrate, can be changed. The mechanical behavior of biological cells can thus be observed at fast temperature jumps.

The apparatus, in particular the laser of the apparatus, can be configured to irradiate the electromagnetic radiation at a wavelength in the range from 400 to 1200 nm, preferably in the range from 500 to 1100 nm, particularly preferably in the range from 600 to 1000 nm, in particular in the range from 700 to 900 nm.

The apparatus, in particular the laser of the apparatus, can furthermore be configured to irradiate the electromagnetic radiation at an intensity in the range from 10 to 4000 mW, preferably 50 to 3000 mW, particularly preferably 200 to 2500 mW, very particularly preferably 1000 to 2000 mW.

In addition, the apparatus, in particular the laser of the apparatus, can be configured to irradiate the electromagnetic radiation in a pulsed manner, preferably at a frequency of 1 to 1000 Hz.

In a preferred embodiment, the apparatus, in particular the laser of the apparatus, is configured to irradiate the electromagnetic radiation for a period in the range from 0.05 to 15 sec., preferably 0.2 to 10 sec., particularly preferably 0.5 to 5 sec., in particular 1 to 2 sec.

The apparatus, in particular the laser of the apparatus, can be configured to irradiate the electromagnetic radiation at an angle to a surface of the substrate in the range from >0° to 90°, preferably in the range from 30° to 90°, particularly preferably in the range from 60° to 90°, very particularly preferably in the range from 80° to 90°, in particular 90°.

The apparatus, in particular the laser of the apparatus, can furthermore be configured to irradiate the electromagnetic radiation with a beam width in the range from 0.1 to 800 μm, preferably in the range from 1 to 600 μm, particularly preferably in the range from 2 to 400 μm, very particularly preferably in the range from 5 to 200 μm, in particular in the range from 10 to 100 μm.

In addition, the apparatus, in particular the laser of the apparatus, can be configured to irradiate the electromagnetic radiation simultaneously or sequentially onto at least one further biological cell, optionally onto a plurality of further biological cells.

The detector for detecting a spatial elongation can be selected from the group consisting of microscope, camera, and combinations thereof, wherein the detector is preferably a high speed camera, wherein a high speed camera is understood as a camera that records 1 to 10,000 frames per second, preferably 2 to 2000 frames per second, particularly preferably 10 to 1000 frames per second, in particular 20 to 500 frames per second.

The at least one biological cell can be selected from the group consisting of prokaryote cell, archaea cell, and eukaryote cell, with the at least one biological cell preferably being a eukaryote cell, optionally a pathogenic eukaryote cell, in particular a eukaryote cell that is selected from the group consisting of epithelial cell, lymphocyte, macrophage, fibroblast, PC12 cell, keratinocyte, and melanoma cell.

In a preferred embodiment of the apparatus in accordance with the invention, the optical axis of the laser and the optical axis of the detector are disposed in a single optical beam path. The apparatus thus needs little space in a direction perpendicular to the two optical axes and can be designed as very compact in this respect.

Furthermore, in accordance with the invention, a method for detecting a spatial elongation of at least one adherent cell is provided, comprising the steps
  a) irradiating at least one biological cell on a substrate with electromagnetic radiation by a laser in a direction of irradiation, wherein the electromagnetic radiation of the laser is selected such that it effects a spatial elongation of the at least one biological cell in a direction parallel to the direction of radiation;
  b) detecting a spatial elongation of the at least one biological cell in a direction parallel to the direction of irradiation via a detector;
characterized in that the at least one biological cell is a biological cell adherent on the substrate.

It is possible for the first time by the method in accordance with the invention to deform a portion of adherent biological cells, a whole adherent biological cell, or a plurality of adherent biological cells spatially- and temporally-selectively, and without contact to a measurement device, via a directly applied stretching force in a direction perpendicular to the substrate and away from the substrate, to detect the degree of deformation, and to derive mechanical properties (e.g. viscoelastic properties via stress-strain curves) of the at least one adherent cell or parts thereof in the natural (i.e. adherent) state of the cell from the degree of deformation.

If the environment of the at least one biological cell turned away from the substrate has a refractive index that is smaller than the refractive index of the cell itself (e.g. air with a refractive index of 1.00 or an aqueous buffer with a refractive index of 1.33), the at least one cell is stretched away from the substrate. If the environment of the at least one biological cell turned away from the substrate has a refractive index that is greater than the refractive index of the cell itself (e.g. glycerin with a refractive index of 1.47), the at least one cell is stretched toward the substrate, i.e. compressed toward the substrate. In both cases, mechanical properties of the at least one adherent cell or parts thereof can be derived by the detected degree of deformation of the at least one adherent cell.

The method in accordance with the invention can be characterized in that no laser is used that irradiates electromagnetic radiation onto the at least one biological cell in a direction that has an angle of 180°, optionally an angle in the range from >90° to 180°, to the direction of irradiation.

In a preferred embodiment, a light source is used in the method and the at least one biological cell is irradiated with light in a direction of light irradiation, wherein the direction of light irradiation is preferably parallel to the direction of irradiation of the laser on the at least one biological cell and/or against the direction of radiation of the laser on the at least one biological cell (i.e. the light source is irradiated at an angle of 180° to the direction of irradiation of the laser onto the at least one biological cell). The light source is preferably selected from the group consisting of light sources of incoherent light, particularly preferably selected from the group consisting of halogen lamp, LED, and combinations thereof.

In a preferred embodiment of the method, the electromagnetic radiation, optionally deflected via a dichroic and/or simple mirror, is radiated onto the at least one biological cell (or portions thereof) perpendicular to a surface of the substrate on which the at least one biological cell is located. The dichroic mirror can be suitable to reflect light having a wavelength of >700 nm (e.g. laser light of the wavelength 800 nm) and to allow light having a wavelength of ≤700 nm (e.g. visible light) to pass. The simple mirror can be suitable to reflect visible light and IR light (e.g. light having a wavelength of 400 nm to 800 nm).

In a particularly preferred embodiment of the method, the electromagnetic radiation is radiated through the substrate onto the at least one biological cell (or parts thereof). It is essential in this case that the substrate allows the electromagnetic radiation of the laser to pass at least in part, with the substrate particularly preferably being transparent for the electromagnetic radiation. The substrate can be selected from the group consisting of glass, quartz glass, quartz, transparent plastic (e.g. PMMA or polycarbonate), and combinations thereof.

In a preferred embodiment, the laser is moved along a surface of the substrate and/or the substrate is moved along a surface of the substrate, preferably along a plane that is parallel to a surface of the substrate. A piezo stage on which the substrate is arranged can be used for this purpose.

A processing unit can be used in the method that receives and evaluates the data of the detector and/or of a data storage of the apparatus, wherein the processing unit preferably carries out a conversion of the data on a spatial elongation of the at least one cell in an unknown length into a spatial elongation of the at least one cell in a known length, wherein the processing unit particularly preferably uses diffraction images detected at the detector and a (calibrated) point spread function for the conversion and wherein the processing unit very particularly preferably converts the data on the spatial elongation into a focal height, an E-modulus, and/or a shear modulus of the at least one biological cell.

It is advantageous for a detection of the relative height change of the at least one cell with high sensitivity if the cell membrane of the at least one cell is marked with a substance that has a greater refractive index than the environment of the at least one cell remote from the substrate, preferably a refractive index that is greater than the refractive index of the at least one cell. For example, particles can be adhered to the cell membrane of the cell(s) for this purpose. The particles can comprise or consist of, for example, a plastic material, preferably polystyrene (refractive index 1.58). The particles preferably have a mean particle diameter in the range from 1 nm to 10 µm, particularly preferably 10 nm to 5 µm, very particularly preferably 100 nm to 2 µm, in particular 1 µm, measured via dynamic light scattering. The at least one cell is in particular marked by 1 to 10, preferably 2 to 9, particularly preferably 4 to 8, particles. The detection sensitivity of the elongation of the at least one cell can thus be considerably increased since the movement of the particles can be detected via the detector and the movement of the (unmarked) cell membrane does not have to be detected via the detector.

For the conversion of the relative height change detected by the detector into an absolute height change, the detector is suitable for being calibrated in a preferred embodiment of the method. In this respect, the substrate is preferably moved in a direction parallel to the direction of irradiation of the laser, particularly preferably over a piezo table on which the substrate is arranged. A specific value of the vertical change can be associated with each detector signal by the moving of the substrate in a direction parallel to the direction of radiation of the laser, and the vertical change of the cell(s), that is only qualitative per se, can be quantified (e.g. given in nanometers to micrometers).

A temperature control unit for the tempering of the substrate can be used in the method. The temperature control unit preferably tempers the substrate to a temperature in the range from >0° C. to <60° C., preferably 5° C. to 50° C., particularly preferably 10° C. to 45° C., in particular 20° C. to 40° C. The substrate used in the method can comprise a channel system through which a cooling fluid of the temperature control unit flows. The substrate used in the method can furthermore have a specific heat capacity of less than 4 J/g·K, preferably less than 3 J/g·K, particularly preferably less than 2 J/g·K, very particularly preferably less than 1 J/g·K, in particular less than 0.5 J/g·K. The lower the specific heat capacity of the substrate, the faster the temperature of the substrate and thus of the cells adherent to the substrate can be changed. The mechanical behavior of biological cells can thus be observed at fast temperature jumps.

In a preferred embodiment, the laser irradiates the electromagnetic radiation at a wavelength in the range from 400 to 1200 nm, preferably in the range from 500 to 1100 nm, particularly preferably in the range from 600 to 1000 nm, in particular in the range from 700 to 900 nm, in the method.

In the method, the laser can furthermore irradiate the electromagnetic radiation at an intensity in the range from 10 to 4000 mW, preferably 50 to 3000 mW, particularly preferably 200 to 3000 mW, very particularly preferably 1000 to 2000 mW.

In addition, in the method, the laser can irradiate the electromagnetic radiation in a pulsed manner, preferably at a frequency of 1 to 1000 Hz.

In a further preferred embodiment, the laser irradiates the electromagnetic radiation for a period in the range from 0.05 to 15 sec., preferably 0.2 to 10 sec., particularly preferably 0.5 to 5 sec., in particular 1 to 2 sec.

The method can be characterized in that the laser irradiates the electromagnetic radiation at an angle to a surface of the substrate in the range from >0° to 90°, preferably in the range from 30° to 90°, particularly preferably in the range from 60° to 90°, very particularly preferably in the range from 80° to 90°, in particular 90°.

The electromagnetic radiation irradiated by the laser can be irradiated with a beam width in the range from 0.1 to 800 µm, preferably in the range from 1 to 600 µm, particularly preferably in the range from 2 to 400 µm, very particularly preferably in the range from 5 to 200 µm, in particular in the range from 10 to 100 µm.

The method can be characterized in that the laser irradiates the electromagnetic radiation simultaneously or sequentially onto at least one further biological cell, optionally onto a plurality of further biological cells.

The detector used in the method for detecting a spatial elongation can be selected from the group consisting of microscope, camera, and combinations thereof, wherein the detector is preferably a high speed camera, wherein a high speed camera is understood as a camera that records 1 to 10,000 frames per second, preferably 2 to 2000 frames per second, particularly preferably 10 to 1000 frames per second, in particular 20 to 500 frames per second.

The at least one biological cell used in the method can be selected from the group consisting of prokaryote cell, archaea cell, and eukaryote cell, with the at least one biological cell preferably being a eukaryote cell, optionally a pathogenic eukaryote cell, in particular a eukaryote cell that is selected from the group consisting of epithelial cell, lymphocyte, macrophage, fibroblast, PC12 cell, keratinocyte, and melanoma cell.

In a preferred embodiment of the method in accordance with the invention, the optical axis of the laser and the optical axis of the detector are brought to lie in a single optical beam path.

The use of the apparatus in accordance with the invention and/or of the method in accordance with the invention for the in vitro diagnosis of a disease is furthermore proposed, wherein the spatial elongation of at least one adherent cell to be diagnosed is preferably determined and is compared for this purpose with a spatial elongation of at least one healthy adherent cell and/or with a spatial elongation of at least one pathological adherent cell.

The subject matter in accordance with the invention will be explained in more detail with reference to the following FIGS. without intending to restrict it to the specific embodiment shown here.

FIGS. 1A-1B show aspects of an embodiment of an apparatus in accordance with the invention. In FIG. 1A, it is shown how the spatial elongation of the biological cell 1 adherent on the substrate 2 takes place. Laser light of a laser 3 is here first deflected via a dichroic mirror onto a (simple) mirror 9. The (simple) mirror 9 in turn deflects the laser light of the laser 3 in the direction or irradiation 4, whereby the laser first passes through an objective 8 and then impacts the biological cell 1 through the (transparent) substrate 2. The biological cell 1 experiences a spatial elongation 5 due to the effect of the laser light. In FIG. 1B, it is shown how the spatial elongation 5 of the biological cell 1 can be detected via the detector 6. In this case, the apparatus additionally comprises a light source 7 for illuminating the cell 1 to amplify the light signal received at the detector 6. The cell 1 is illuminated by this light source 7 parallel to the direction of irradiation 4. The light deflected by the cell first passes through the (transparent) substrate 2 and then the objective to then impact the (simple) mirror 9. The (simple) mirror deflects the light of the cell 1 onto the dichroic mirror 10 that allows the light originating from the light source 7 to pass through and to impact the detector 6.

REFERENCE NUMERAL LIST

1: biological cell;
2: substrate;
3: laser;
4: direction of irradiation;
5: spatial elongation of the biological cell;
6: detector for detecting a spatial elongation of the cell;
7: light source to illuminate the cell;
8: objective;
9: mirror;
10 dichroic mirror.

The invention claimed is:

1. An apparatus for detecting a spatial elongation of at least one adherent cell, comprising
   (a) at least one biological cell on a substrate;
   (b) a laser for irradiating the at least one biological cell with electromagnetic radiation in a direction of irradiation, wherein the laser is configured to irradiate electromagnetic radiation on the at least one biological cell that effects a spatial elongation of the at least one biological cell in a direction parallel to the direction of irradiation; and
   (c) a detector for detecting a spatial elongation of the at least one biological cell in a direction parallel to the direction of irradiation;
   wherein the at least one biological cell is a biological cell adherent on the substrate, and
   wherein the laser is configured to irradiate the electromagnetic radiation at a power in the range from 50 to 2000 mW,
   wherein the apparatus has a processing unit that is configured to receive and evaluate data of the detector and/or of a data storage of the apparatus, and
   wherein the processing unit is configured to carry out a conversion of the data on a spatial elongation of the at least one cell in an unknown length into a spatial elongation of the at least one cell in a known length, wherein the processing unit is configured to utilize, for carrying out the conversion, diffraction images detected at the detector and a point spread function.

2. The apparatus in accordance with claim 1, wherein the apparatus does not have a laser that is configured to irradiate electromagnetic radiation onto the at least one biological cell in a further direction that has an angle of 180°, optionally an angle in the range from >90° to 180°, to the direction of irradiation.

3. The apparatus in accordance with claim 1, wherein the apparatus is configured to move the laser along a surface of the substrate and/or to move the substrate along a surface of the substrate.

4. The apparatus in accordance with claim 1, wherein the processing unit is configured to receive and evaluate data of the detector and/or of a data storage of the apparatus.

5. The apparatus in accordance with claim 1, wherein the apparatus comprises a temperature control unit for tempering of the substrate.

6. The apparatus in accordance with claim 5, wherein
   (i) the temperature control unit is configured to temper the substrate to a temperature in the range from >0° C. to <60° C.; and/or
   (ii) the substrate comprises a channel system through which a cooling fluid of the temperature control unit can flow; and/or
   (iii) the substrate has a specific heat capacity of less than 4 J/g·K.

7. The apparatus in accordance with claim 1, wherein the apparatus is configured to irradiate the electromagnetic radiation
   (i) at a wavelength in the range from 400 to 1200 nm; and/or
   (ii) in a pulsed manner; and/or
   (iii) for a period in the range from 0.05 to 15 sec; and/or
   (iv) at an angle to a surface of the substrate in the range from >0° to 90°; and/or
   (v) with a beam width in the range from 0.1 to 800 μm; and/or
   (vi) simultaneously or sequentially onto at least one further biological cell, optionally onto a plurality of further biological cells.

8. The apparatus in accordance with claim 1, wherein the detector for detecting a spatial elongation is selected from the group consisting of microscope, camera, and combinations thereof.

9. The apparatus in accordance with claim 1, wherein the at least one biological cell is selected from the group consisting of prokaryote cell, archaea cell, and eukaryote cell.

10. A method for detecting a spatial elongation of at least one adherent cell, comprising:

(a) irradiating at least one biological cell on a substrate with electromagnetic radiation by a laser in a direction of irradiation, wherein the electromagnetic radiation of the laser is selected such that it effects a spatial elongation of the at least one biological cell in a direction parallel to the direction of irradiation; and (b) detecting a spatial elongation of the at least one biological cell in a direction parallel to the direction of irradiation via a detector;

wherein the at least one biological cell is a biological cell adherent on the substrate, wherein the laser irradiates the electromagnetic radiation at a power in the range from 50 to 2000 mW, wherein, in the method, a processing unit that receives and evaluates data of the detector is utilized, and wherein the processing unit carries out a conversion of the data on a spatial elongation of the at least one cell in an unknown length into a spatial elongation of the at least one cell in a known length, wherein, for carrying out the conversion of the data, the processing unit utilizes diffraction images detected at the detector and a point spread function.

11. The method in accordance with claim 10, wherein no laser is used in the method that irradiates electromagnetic radiation onto the at least one biological cell in a direction that has an angle of 180°, optionally an angle in the range from >90° to 180°, to the direction of irradiation.

12. The method in accordance with claim 10, wherein the laser is moved along a surface of the substrate and/or the substrate is moved along a surface of the substrate, preferably along a plane that is parallel to a surface of the substrate.

13. The method in accordance with claim 10, which utilizes a temperature control unit for tempering the substrate.

14. The method in accordance with claim 10, wherein the laser irradiates electromagnetic radiation
   (i) at a wavelength in the range from 400 to 1200 nm; and/or
   (ii) in a pulsed manner; and/or
   (iii) for a period in the range from 0.05 to 15 sec.; and/or
   (iv) at an angle to a surface of the substrate in the range from >0° to 90°; and/or
   (v) with a beam width in the range from 0.1 to 800 µm; and/or
   (vi) simultaneously or sequentially onto at least one further biological cell, optionally onto a plurality of further biological cells.

15. The method in accordance with claim 10, wherein the detector for detecting a spatial elongation is selected from the group consisting of microscope, camera, and combinations thereof.

16. The method in accordance with claim 10, wherein the at least one biological cell is selected from the group consisting of prokaryote cell, archaea cell, and eukaryote cell.

17. A method of conducting in vitro diagnosis of a disease in a person, the method comprising utilizing an apparatus according to claim 1, and comprising the following steps:
   (a) providing at least one adherent biological cell of the person on the substrate of the apparatus, irradiating the at least one adherent biological cell on the substrate with electromagnetic radiation by the laser of the apparatus in a direction of irradiation and at a power in the range from 50 to 2000 mW, and detecting a spatial elongation of the at least one adherent biological cell to be diagnosed in a direction parallel to the direction of irradiation via the detector of the apparatus; and
   (b) providing at least one pathological adherent biological cell of the person on the substrate of the apparatus, irradiating the at least one pathological adherent biological cell on the substrate with electromagnetic radiation by the laser of the apparatus in a direction of irradiation and at a power in the range from 50 to 2000 mW, and detecting a spatial elongation of the at least one pathological adherent biological cell in a direction parallel to the direction of irradiation via the detector of the apparatus;
   (c) comparing the detected spatial elongation of the at least one adherent biological cell to be diagnosed with the detected spatial elongation of the at least one pathological adherent biological cell; and
   (d) diagnosing that the person has a disease if the comparison reveals that the detected spatial elongation of the at least one adherent biological cell to be diagnosed corresponds to the detected spatial elongation of the at least one pathological adherent biological cell.

* * * * *